United States Patent
Cheng et al.

(10) Patent No.: US 6,438,401 B1
(45) Date of Patent: Aug. 20, 2002

(54) INDENTIFICATION AND QUANTIFICATION OF NEEDLE DISPLACEMENT DEPARTURES FROM TREATMENT PLAN

(75) Inventors: Gang Cheng; Haisong Liu; Yan Yu, all of Rochester, NY (US)

(73) Assignee: Alpha Intervention Technology, Inc., Rochester, NY (US)

( * ) Notice: Subject to any disclaimer, the term of this patent is extended or adjusted under 35 U.S.C. 154(b) by 0 days.

(21) Appl. No.: 09/636,551

(22) Filed: Aug. 11, 2000

Related U.S. Application Data

(60) Provisional application No. 60/200,493, filed on Apr. 28, 2000.

(51) Int. Cl.[7] .............................................. A61B 5/05
(52) U.S. Cl. ........................... 600/407; 128/898; 600/1; 600/3; 600/7; 600/8
(58) Field of Search ................................ 600/407, 1, 3, 600/7, 8; 128/898

(56) References Cited

U.S. PATENT DOCUMENTS

| | | | | |
|---|---|---|---|---|
| 4,976,680 A | * | 12/1990 | Hayman et al. ................ 600/7 |
| 5,107,839 A | * | 4/1992 | Houdek et al. ............. 606/130 |
| 5,391,139 A | | 2/1995 | Edmundson | |
| 6,032,066 A | * | 2/2000 | Lu et al. ..................... 600/407 |
| 6,083,167 A | * | 7/2000 | Fox et al. .................... 600/439 |
| 6,167,294 A | * | 12/2000 | Busch ......................... 600/425 |
| 6,200,255 B1 | * | 3/2001 | Yu ................................ 600/1 |
| 6,234,951 B1 | * | 5/2001 | Hastings ........................ 600/3 |
| 6,256,529 B1 | * | 7/2001 | Holupka et al. ............. 600/427 |
| 6,273,858 B1 | * | 8/2001 | Fox et al. .................... 600/466 |

FOREIGN PATENT DOCUMENTS

WO     WO 00/25865     5/2000

* cited by examiner

*Primary Examiner*—Marvin M. Lateef
*Assistant Examiner*—Runa Shah Qaderi
(74) *Attorney, Agent, or Firm*—Blank Rome Comisky & McCauley LLP

(57) ABSTRACT

A placement plan is developed for the placement of radioactive seeds in a prostrate for brachytherapy. The placement plan is made available to an intraoperative tracking interface which also shows a live ultrasound image of the needle or catheter placement in the prostate. The difference in the x-y plane between the planned and actual locations of the needle or catheter is calculated, and from that difference, the error in position of each seed is calculated. The seeds are moved, or the operator changes the number of seeds, and the dose is recalculated. A small column of ultrasound images is taken, and each seed located in the column of images is given a confidence level. If the confidence level exceeds a threshold set by the operator, the dosimetry is recalculated. Periodically throughout the seed placement, fluoroscopic x-rays are taken, and the seed coordinates are matched to the x-ray image. Seed locations with low confidence levels are adjusted based on the x-ray locations, and the dosimetry is recalculated.

33 Claims, 9 Drawing Sheets

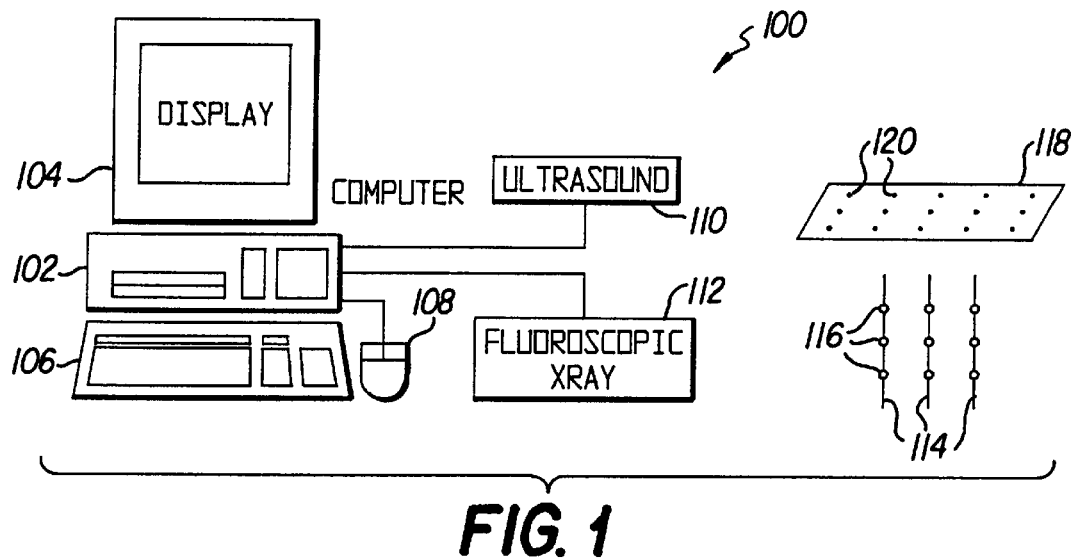
FIG. 1
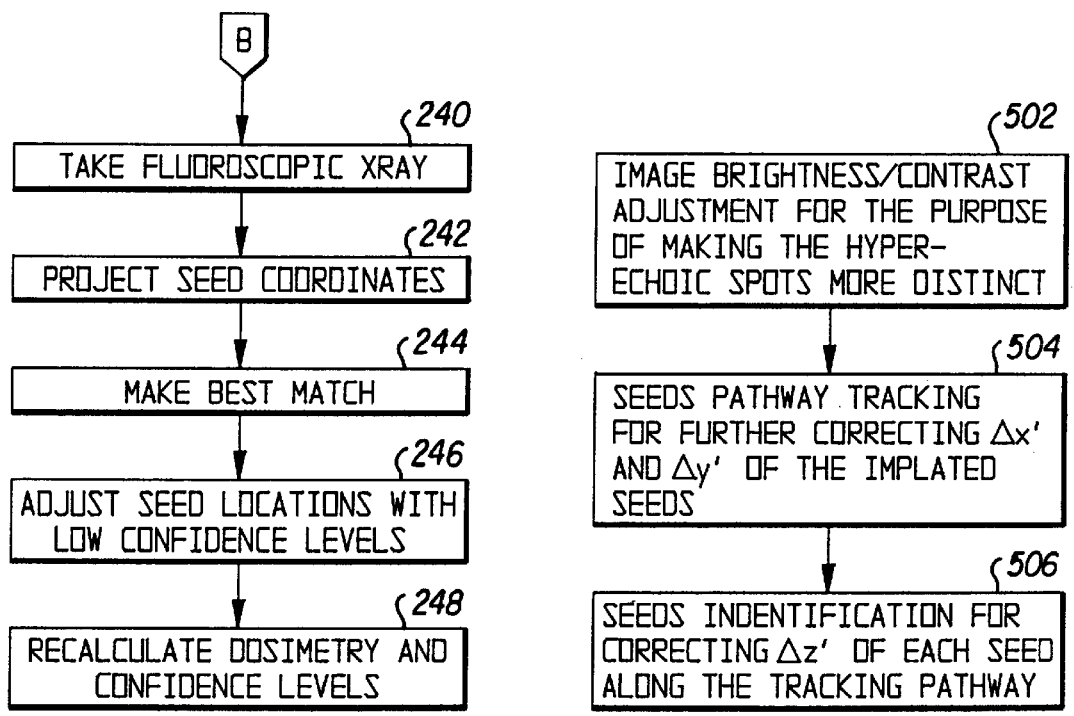
FIG. 2C
FIG. 5

INDENTIFICATION AND QUANTIFICATION OF NEEDLE DISPLACEMENT DEPARTURES FROM TREATMENT PLAN

REFERENCE TO RELATED APPLICATION

The present application claims the benefit of U.S. Provisional Application No. 60/200,493, filed Apr. 28, 2000, whose disclosure is hereby incorporated by reference in its entirety into the present disclosure.

FIELD OF THE INVENTION

The present invention is directed to an improvement to treatment plans using brachytherapy or the like and more specifically to a technique for rapid and accurate identification and quantification of needle placement departures from such a treatment plan.

DESCRIPTION OF RELATED ART

In the treatment of prostate cancer, a method is often employed to implant numerous radioactive seeds in a carefully preplanned pattern in three dimensions within the prostate. That procedure serves to deliver a known amount of radiation dosage concentrated around the prostate, while at the same time sparing radiation-sensitive tissues, such as the urethra, the bladder and the rectum. Customarily, 60 to 120 seeds are placed through 15 to 30 needles in the inferior (feet) to superior (head) direction. Those needle positions are selected from a 13×13 grid of 0.5 cm evenly spaced template holes, which are used to achieve precise needle insertion. The number of those holes which intersect with the prostate cross section, and therefore are potentially usable, is typically about 60. The number of mathematical combinations is therefore greatly in excess of $10^{16}$, each of which is a potential treatment plan but is associated with different degrees of cancer control and a different likelihood of treatment complications.

In current clinical practice, the design of a suitable seed configuration which is customized to the anatomy of a patient is achieved by a highly trained medical physicist or dosimetrist by using trial-and-error manual iterations. The practitioner usually starts with an initial needle configuration based on experience or rules of thumb, and then adjusts the radioactive strength per seed or the locations of certain needles or both until the calculated dose intensity distribution satisfies a set of clinical considerations. That process requires between 15 minutes and 2 hours, depending on the experience of the treatment planner and the geometric complexity of the relationship between the prostate and the surrounding anatomical structures.

Those known treatment planning processes are typically aided by one of several available commercial computerized treatment planning systems. Such treatment planning systems enable the user to outline the prostate in relation to a template grid, to turn on or off any available needle positions and seed positions within each needle, and to examine the resultant dose distribution in two or three dimensions. Examples of such planning systems include those offered by Multimedia Medical Systems (MMS) of Charlottesville, Va., SSGI Prowess, of Chico, Calif., Nucletron Plato, from Columbia, Md., Computerized Medical Systems (CMS) Focus, of St Louis, Mo., Radiation Oncology Computer Systems (ROCS), of Carlsbad, Calif., ADAC Laboratory's Pinnacle, of Milpitas, Calif. and Theraplan, available from Theratronics International Ltd. of Kanata, Ontario, Canada.

In a number of such known commercial treatment planning systems, for example, those available from MMS and SSGI, the initial needle configuration that otherwise would have to be turned on by the human treatment planner is automatically set up by the computer system. That initial setup is based on simple rules of thumb, such as uniform loading, peripheral loading or modified peripheral loading. In a number of instances, the manufacturer claims that its planning system offers "automatic planning", "geometric optimization", or "real-time dosimetry". However, none of those commercial planning systems offer true optimization in that the automatically loaded seeds are not designed based on customized dosimetric calculations. Rather, they are designed to fill the space of the prostate in some predetermined manner. Therefore, such known automatic seed loading techniques are designed to save between 15 and 30 mouse clicks by the operator (or about 1 minute of operation). However, the user is still required to apply his or her expert knowledge to iteratively improve upon that initial design in order to achieve customized planning for any individual patient. Thus, there are two significant drawbacks of the above-mentioned current techniques: First, the complete treatment planning process is under the manual guidance of a radiation planning expert using trial and error techniques; and second, the adjustment of the delivered dose is achieved by varying the radioactive strength per seed until an isodose surface with the desired shape and size is scaled up or down to the prescription dose, i.e., those techniques will suffer when the activity per seed is fixed, as at the time of surgical implantation in the operating suite.

Because of those two severe drawbacks, the currently available commercial treatment planning systems are not suitable for intraoperative treatment planning in the surgical suite, where the patient is placed under anesthesia in volatile conditions and where the cost per minute is very high. The variability of human performance, experience and stress, and the general inability of humans to manage large amounts of numerical data in 1 to 2 minutes are also factors that deter current practitioners from performing intraoperative treatment planning.

An optimization technique for treatment planning is taught by U.S. Pat. No. 5,391,139 to Edmundson. More specifically, Edmundson is intended for use with a high dose rate (HDR) source which is moved within a hollow needle implanted in a prostate or other anatomical portion. The medical personnel using the system of Edmundson select a needle location using empirically predetermined placement rules. An image is taken of the prostate with the hollow needles implanted in it, and the dwell time of the source at each dwell position in the needle is optimized. However, placement itself is not optimized, but must instead be determined by a human operator.

Another optimization technique is taught by WO 00/25865 to one of the inventors of the present invention. An implant planning engine plans implants for radiotherapy, e.g., prostrate brachytherapy. The system optimizes intraoperative treatment planning on a real-time basis using a synergistic formulation of a genetic algorithm, multi-objective decision theory and a statistical sensitive analysis.

While the above techniques allow calculation of optimized dwell time, placement or the like, they do not provide for detection and correction of errors in needle or seed placement.

SUMMARY OF THE INVENTION

It will be apparent from the above that a need exists in the art to detect and correct errors in implementation of a treatment plan.

It is therefore a primary object of the present invention to permit rapid and accurate identification and quantification of needle placement departures from a treatment plan generated prior to a brachytherapy implant based on real-time ultrasound.

It is another object of the invention to allow real-time correction to the brachytherapy dosimetry and iterative compensation of loss of dose coverage due to misplacement of the needles/catheters and seeds.

It is still another object of the invention to permit such identification, quantification and correction without the need for CT or MR imaging during the interval between needle/catheter placement in the target organ and final deposition of radioactive sources for irradiation of the target organ.

To achieve the above and other objects, the present invention is directed to a technique for identifying and quantifying needle displacement departures from a placement plan for the placement of radioactive seeds in a prostrate or other internal organ for brachytherapy or the like. The placement plan is made available to an intraoperative tracking interface which also shows a live ultrasound image of the needle or catheter placement in the prostate. The difference in the x-y plane between the planned and actual locations of the needle or catheter is calculated, and from that difference, the error in position of each seed is calculated. The seeds are moved, or the operator changes the number of seeds, and the dose is recalculated. A small column of ultrasound images is taken, and each seed located in the column of images is given a confidence level. If the confidence level exceeds a threshold set by the operator, the dosimetry is recalculated. Periodically throughout the seed placement, fluoroscopic x-rays are taken, and the seed coordinates are matched to the x-ray image. Seed locations with low confidence levels are adjusted based on the x-ray locations, and the dosimetry is recalculated.

In a preferred embodiment, the technique is carried out through the following steps.

1. The needle/catheter placement plan is made available to an intraoperative tracking interface. That interface contains an electronic worksheet of needle and seed coordinates, a live ultrasound image window into which real-time video image of needle/catheter placement is fed, and a series of isodose dosimetry panels reflecting the current state of dose coverage. Each of the needles/catheters can be activated by highlighting the corresponding row in the coordinates worksheet, or by highlighting the corresponding grid location graphically.

2. Following insertion of each needle/catheter, a hyperechoic (i.e., bright) spot appears on the live ultrasound image. That location is manually identified by the operator. The difference in the x-y plane between the planned location and the actual location of the needle/catheter is calculated to give errors $\Delta x$ and $\Delta y$. The errors $\Delta x$ and $\Delta y$ are then reflected on the grid location. The errors of each seed, $\Delta x'$ and $\Delta y'$, are calculated based on straight line interpolation at the planned z location of the seed; the said straight line is constructed by joining two known points: (a) the actual needle location shown on ultrasound at the known z plane, (b) the template coordinate outside the patient body, through which the needle is inserted under precision template guidance (therefore at that location $\Delta x$ and $\Delta y$ shall be assumed to equal zero). The dose is then recalculated by moving the seeds along the activated needle/catheter in x and y by amounts $\Delta x'$ and $\Delta y'$, which may be the same or different for each and every seed. The dosimetry updated by such feedback of seed placement errors is redisplayed on the series of isodose panels.

In addition, the operator is permitted to change the number of seeds deposited by the needle/catheter in question. In that case, the operator is required to enter the seed locations along the needle/catheter, which overrides the original treatment plan. Seed placement errors in such a case are tracked identically to the procedure described above.

3. A small column of ultrasound images in 3D is acquired along the straight line as constructed above. That column can be perpendicular to the x-y plane, or in fact may often sustain an angle $\alpha$ and an angle $\beta$ from the x and the y planes, respectively. The exact number of seeds as deposited is identified using image processing algorithms in that column of 3D ultrasound region of interest. Each seed identified in that manner is assigned a confidence level, which depicts the likelihood/uncertainty of seed localization. The size of that column is initially set small; if the total number of seeds found in that manner is not equal to the number of seeds deposited by the given needle/catheter, the width of the column is adjusted (e.g., the width is increased to find additional seeds).

Whereas the previous step quantifies the errors $\Delta x'$ and $\Delta y'$ for each seed, the ultrasound step quantifies $\Delta z'$ for each seed and at the same time further corrects $\Delta x'$ and $\Delta y'$. If the confidence level of a given seed's localization exceeds a threshold value (to be set by the operator), the dosimetry is re-calculated yet again using the updated seed location and displayed in the same isodose panels. The isodose calculated is assigned a confidence level, which is a numerical composite of the individual confidence levels of the seeds and the dosimetric impact of positional uncertainties at each seed location (e.g., in high dose region, positional uncertainty has low impact).

4. Periodically throughout the seed placement procedure and the end of seed placement, a fluoroscopic x-ray may be may be taken in the anterior-posterior direction and at up to $\pm 45$ degrees on either side of the anterior-posterior directions. The seed coordinates as determined above are projected in the same orientations. A best match to the x-ray seed projections is made based on multiple point matching using those seed identifications with the highest confidence levels. Subsequent to such matching, the seed locations with low confidence levels are adjusted based on the x-ray locations. As a result, the confidence levels of those latter seeds are increased by a amount reflective of the best match quality. The dosimetry is recalculated. The confidence level of the dosimetry is updated using updated confidence levels of the seeds.

BRIEF DESCRIPTION OF THE DRAWINGS

A preferred embodiment of the present invention will be set forth in detail with reference to the drawings, in which:

FIG. 1 shows a schematic diagram of a system for carrying out the preferred embodiment of the present invention;

FIGS. 2A–2C show a flow chart of a process according to the preferred embodiment;

FIG. 5 shows a flow chart of an image processing technique used to identify seeds in the ultrasound images;

DETAILED DESCRIPTION OF THE PREFERRED EMBODIMENT

Figure 2A:
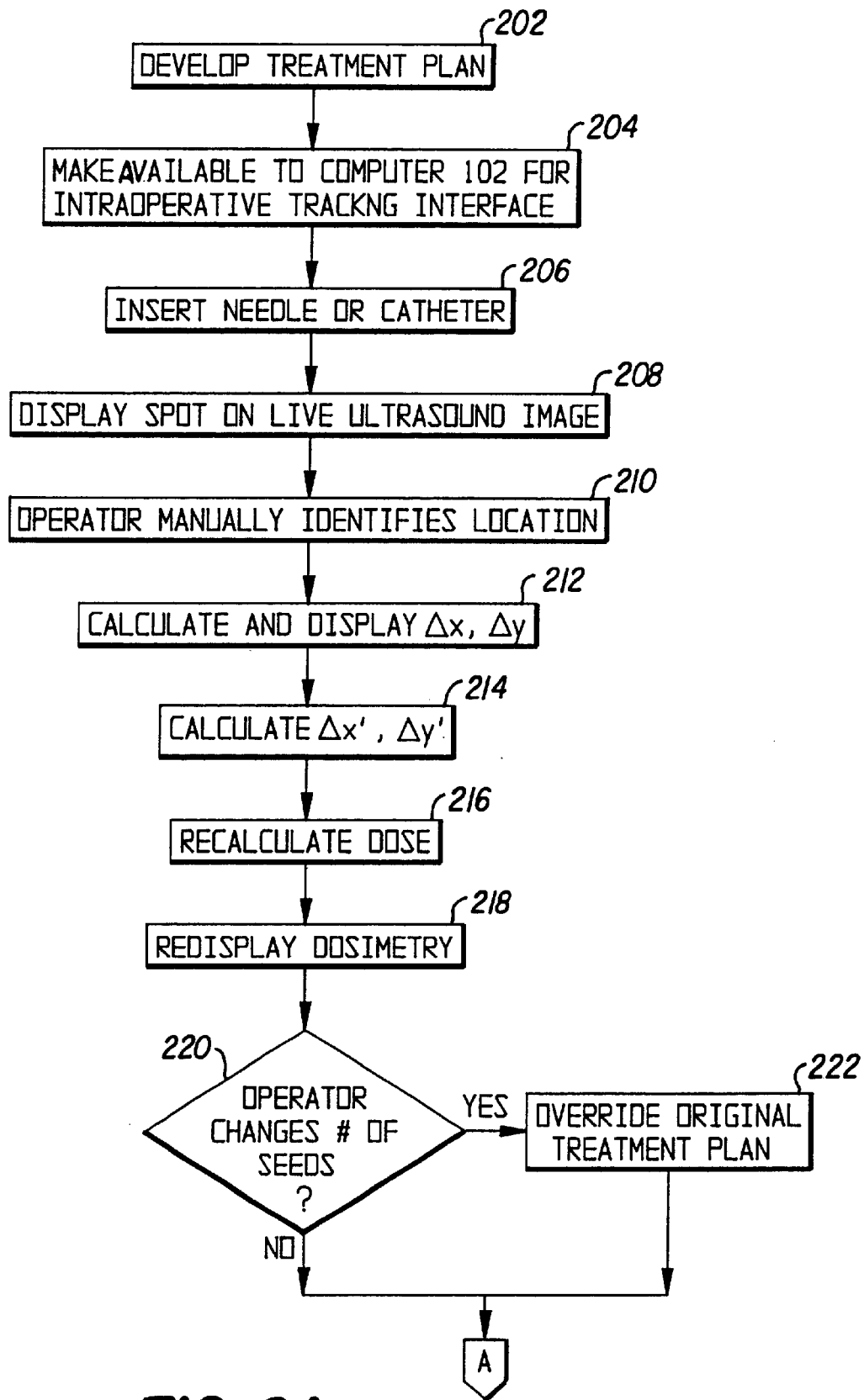

A preferred embodiment of the present invention will be set forth in detail with reference to the drawings, in which like reference numerals refer to like elements throughout.

FIG. 1 shows a system 100 on which the preferred embodiment can be implemented. The system 100 includes a computer 102, which can be the same as the computer used in either of the above-cited Edmundson and Yu references or any other suitable device. The computer uses a display 104 and a user input device or devices such as a keyboard 106 and a mouse 108. Other input devices can be used; for example, the mouse 108 can be replaced by a light pen for use with the display 104. The computer also receives input from an ultrasound device 110 and a fluoroscopic x-ray device 112.

The system also includes components for administering the brachytherapy to the patient. Those components include needles 114 having radioactive seeds 116 spaced therealong in accordance with a treatment plan. A template 118 having a grid of holes 120 is used to position the needles 114 for insertion into the patent's prostate. The specifics of the needles 114, the seeds 116 and the template 118 are known from the prior art cited above. The needles 114 can be replaced by hollow needles or catheters in accordance with the treatment plan to be used.

Figure 2B:
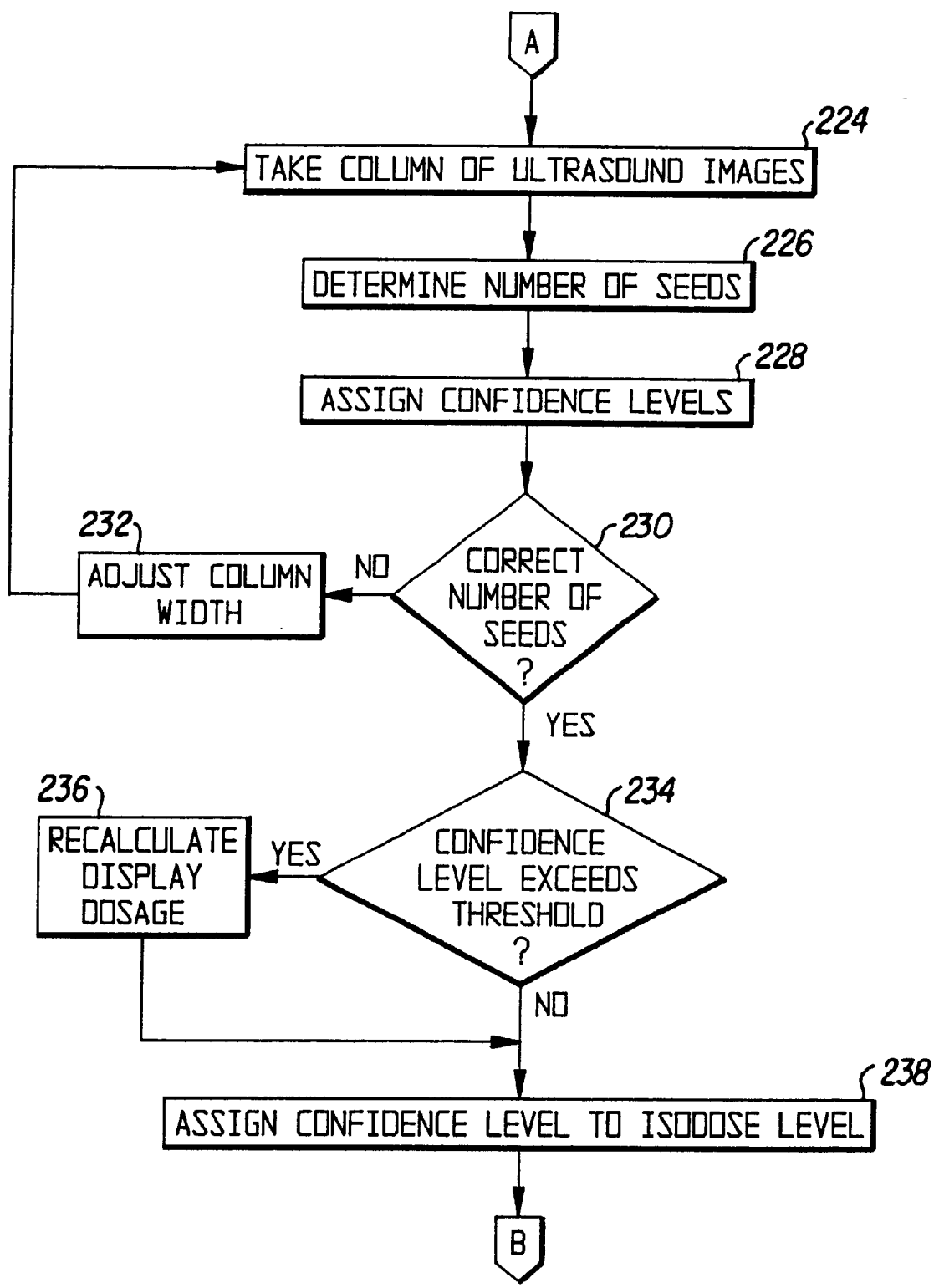

The use of the system 100 will now be explained with reference to the flow chart of FIGS. 2A–2C. In step 202, a treatment plan is developed. Such a treatment plan can be the one developed in the above-cited Yu reference and can be developed either on the computer 102 or on a different device. In step 204, the treatment plan is made available to an intraoperative tracking interface implemented on the computer 102. If the treatment plan is not developed on the computer 102, an appropriate communication medium can be provided to supply the treatment plan to the computer 102.

Figure 3:
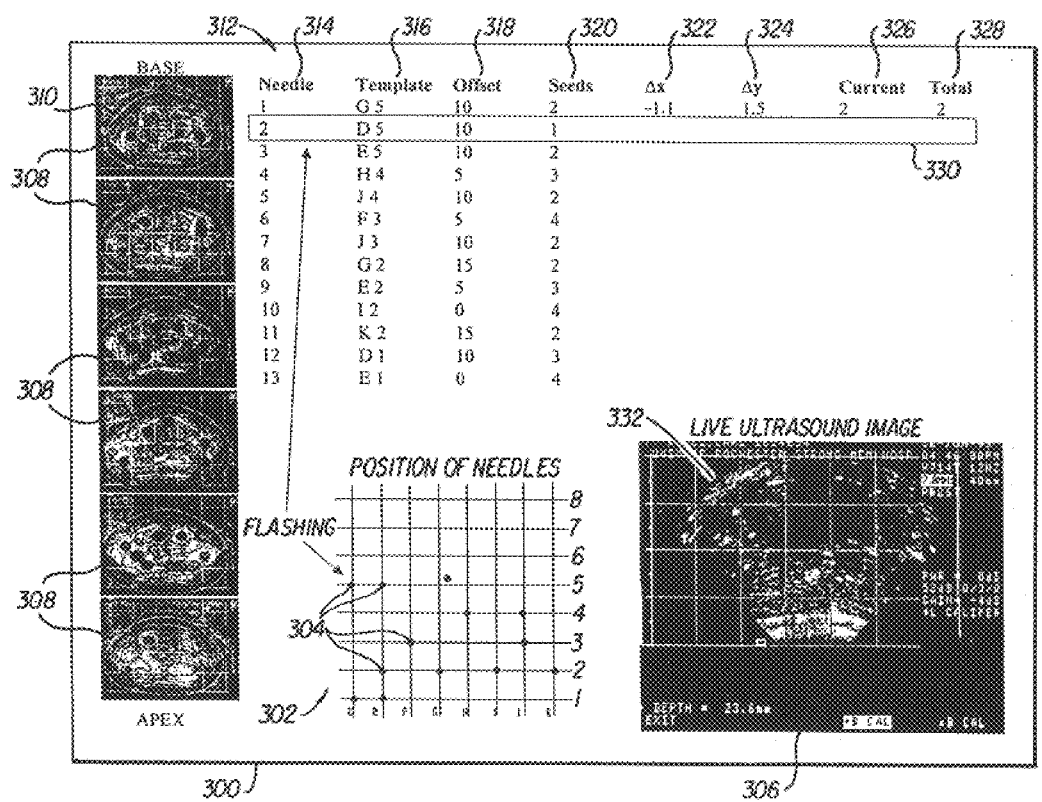
FIG. 3 shows a user interface used in the preferred embodiment.

The intraoperative tracking interface is displayed to the user on the display 104. As shown in FIG. 3, the intraoperative tracking interface 300 includes the following components. An electronic worksheet 302 shows needle and seed coordinates, based on the grid of holes 120 in the template 118, and identifies needle locations with dots 304. A live ultrasound image window 306 shows a real-time image of a section of the prostate obtained from the ultrasound device 110 and allows a real-time view of needle placement in the prostate. From the placement of the seeds, the dosimetry is calculated, and a series of dosimetry panels 308 are shown, each showing the dosimetry in a respective slice of the prostate from the base to the apex. The dosimetry in the panels 308 is shown by isodose lines 310. The electronic worksheet 302 further includes a spreadsheet 312 in which each row indicates one of the needles. The spreadsheet 312 includes a column 314 indicating a needle by a number, a column 316 identifying the hole 120 in the template 118 into which that needle is inserted by its coordinates (letter and number), a column 318 indicating an offset, a column 320 indicating the number of seeds on the needle, a column 322 indicating a $\Delta x$ offset of the needle from its planned position, a column 324 indicating a $\Delta y$ offset of the needle from its planned position, a column 326 indicating the number of currently selected seeds whose offsets have been calculated and a column 328 indicating a total number of seeds whose offsets have been calculated. A needle position 304 which the operator has selected is shown on the interface 300 as flashing, as is the corresponding row 330 in the spreadsheet 312.

Figure 4:
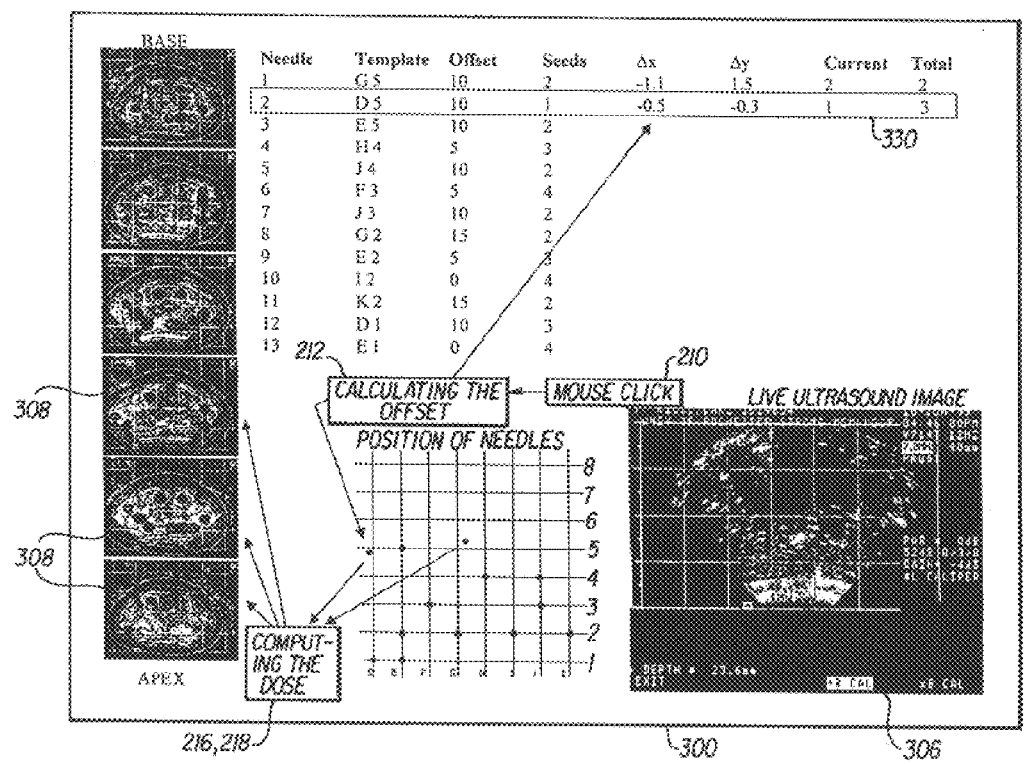
FIG. 4 shows the user interface of FIG. 3 after the calculation of a needle offset and also identifies certain process steps of FIG. 2A with certain components of the user interface.

Following the insertion of each needle or catheter in step 206, the live ultrasound image 306 of the interface 300 displays a bright (hyperechoic) spot 332 in step 208. In step 210, the operator manually identifies the spot 332, e.g., by clicking on it with the mouse 108. In step 212, the he difference in the x-y plane between the planned location and the actual location of the needle or catheter is calculated to give errors $\Delta x$ and $\Delta y$, which are shown both on the grid 302 and on the highlighted row 330 of the spreadsheet. The positional errors in the x-y plane of each seed, $\Delta x'$ and $\Delta y'$, are calculated in step 214 based on straight line interpolation at the planned z location of the seed. The straight line used in the interpolation is constructed by joining two known points: (a) the actual needle location shown on ultrasound at the known z plane and (b) the template coordinate outside the patient body through which the needle is inserted under precision template guidance. At the template 118, $\Delta x$ and $\Delta y$ are assumed to equal zero. The dose is then recalculated in step 216 by moving the seeds along the activated needle or catheter in the x and y directions by those amounts $\Delta x'$ and $\Delta y'$, which may be the same or different for every seed. The dosimetry updated by such feedback of seed placement errors is redisplayed in step 218 on the series of isodose panels 308. FIG. 4 shows the updated interface 300 and also identifies some of the above-mentioned method steps in association with the corresponding elements of the interface 300.

In addition, the operator is permitted to change the number of seeds deposited by the needle or catheter in question in step 220. In that case, the operator is required to enter the seed locations along the needle or catheter, which overrides the original treatment plan in step 222. Seed placement errors in such a case are tracked identically to the procedure described above.

In step 224, a small column of 3D ultrasound images is acquired along the straight line constructed in step 214. That column can be perpendicular to the x-y plane or may be at a non-right angle from the x and/or the y planes. The exact number of seeds as deposited is identified in step 226, using image processing algorithms to be described below, in the column of 3D ultrasound images. Each seed identified in the ultrasound images is assigned a confidence level in step 228, which indicates the likelihood or uncertainty of seed localization.

The size of the column is initially set small. If it is determined in step 230 that the total number of seeds found in step 226 is not equal to the number of seeds deposited by the given needle or catheter, the width of the column is adjusted in step 232; for instance, the width is increased to find additional seeds.

Thus. $\Delta z'$ is quantified for each seed, and at the same time, $\Delta x'$ and $\Delta y'$ are further corrected. If it is determined in step 234 that the confidence level of a given seed's localization exceeds a threshold value (set by the operator), the dosimetry is re-calculated yet again in step 236 using the updated seed location and displayed in the same isodose panels. The isodose calculated is assigned a confidence level in step 238, which is a numerical composite of the individual confidence levels of the seeds and the dosimetric impact of positional uncertainties at each seed location. For example, in a high dose region, positional uncertainty has low impact.

Periodically throughout the seed placement procedure and the end of seed placement, a fluoroscopic x-ray image may be may be taken in step 240 in the anterior-posterior direction and at up to ±45 degrees on either side of the anterior-posterior direction. The seed coordinates as determined above are projected in the same orientations in step 242. A best match to the x-ray seed projections is made in step 244 based on multiple point matching using those seed identifications with the highest confidence levels. Subsequent to such matching, the seed locations with low confidence levels are adjusted in step 246 based on the x-ray locations. As a result, the confidence levels of those latter seeds are increased by a amount reflective of the best match quality. In step 248, the dosimetry is recalculated, and the confidence level of the dosimetry is updated using the updated confidence levels of the seeds.

The image processing algorithms used in carrying out step 226 will now be explained. As shown in the flow chart of FIG. 5, there are three basic steps. In step 502, which is a preprocessing step, the image brightness and contrast are adjusted to make the hyperechoic spots more distinct. In step 504, the seed pathway is tracked for further correcting the offsets $\Delta x'$ and $\Delta y'$ of the implanted seeds. In step 506, the seeds are identified for correcting $\Delta z'$ for each seed along the tracking pathway.

Figure 6A:
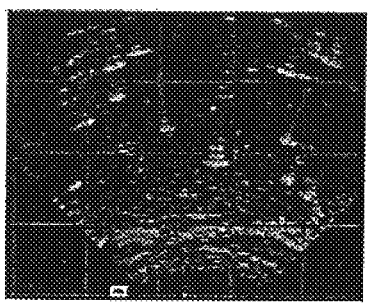
FIGS. 6A and 6B show an image with a desired grayscale distribution and a histogram of the desired grayscale distribution, respectively.

Step 502 involves executing a grayscale transformation to each image in the ultrasound series from apex to base and is thus a pre-processing step. The purpose of step 502 is to adjust the brightness and contrast of the images so that the hyper-echoic spots will be more distinct in the transformed images. According to experience aquired from many actual OR cases, an image suitable for seed recognition processing has a grayscale histogram similar to that shown in FIGS. 6A and 6B, whereas in most cases, the images as taken have grayscale histograms similar to that shown in FIGS. 7A and 7B.

Figure 6B:
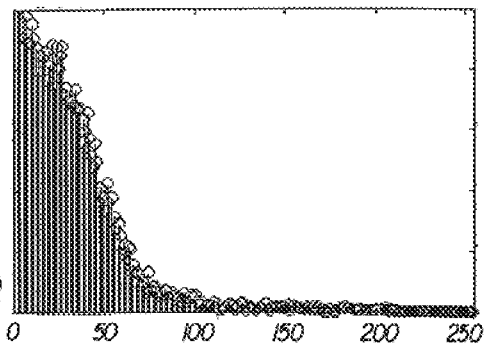

As shown in FIG. 6B, it is preferred that the background be very dark while the hyperechoic spots be very distinct. For that prefered case, 50% of the pixels have grayscale levels below 30, representing the background and dark issues; 90% of the pixels have grayscale levels below 60, with grayscale levels between 30 and 60 most likely representing the brighter issues of the gland; and 95% of the pixels have grayscale levels below 80, with levels between 60 and 80 most likely representing some much brighter issues and some weaker airgaps. The pixels with the highest grayscale levels (from 80 to 255) are the hyper-echoic spots of seeds and some stronger air gaps.

Here, the images are assumed to have an eight-bit grayscale depth, namely, with grayscale values from zero to 255 inclusive. Of course, other grayscale depths can be used instead.

Figure 7A:
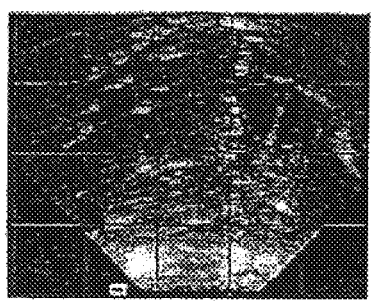
FIGS. 7A and 7B show an image with a typical grayscale distribution and a histogram of the typical grayscale distribution, respectively.
Figure 7B:
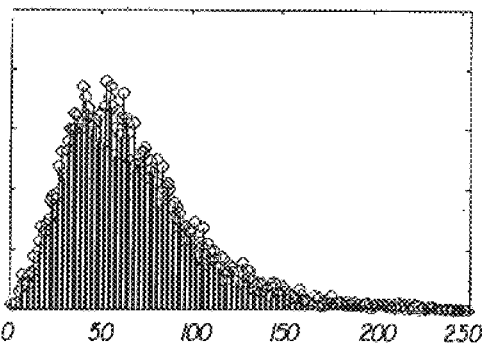

In the images as taken, the 50%, 90% and 95% grayscale levels are higher than the preferred ones set forth above. In the example of FIGS. 7A and 7B, they are 60, 110 and 135, respectively.

To transform an image as taken into an image as preferred, the following grayscale transformation scheme can be used:

| Original image | Transformed image |
|---|---|
| Below median (0~50%) | 1 |
| 50%~90% | 1~50 |
| 90%~95% | 51~75 |
| 95%~100% | 76~255 |

Figure 8A:
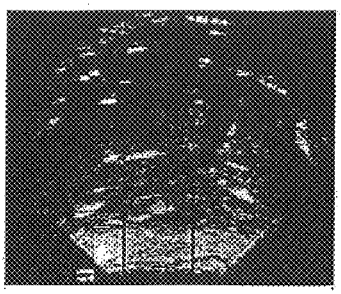
FIGS. 8A and 8B show the image of FIG. 7A after preprocessing and a histogram of the resulting grayscale distribution, respectively.
Figure 8B:
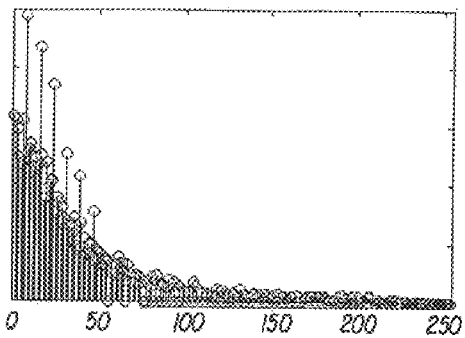

When the image of FIGS. 7A and 7B is subjected to such a transformation, the result is as shown in FIGS. 8A and 8B. A comparison of FIGS. 7A and 7B with FIGS. 8A and 8B shows that the hyper-echoic spots in transformed image of FIGS. 8A and 8B are more distinct than they are in the original image of FIGS. 7A and 7B. Thus, it is easier for the subsequent algorithms to track and identify the seeds. More importantly, it is possible for the algorithms to use unified parameters to process cases with different brightness and contrast settings.

Step 504, automatic tracking of the seeds along a same needle, is used to correct $\Delta x'$ and $\Delta y'$ (displacement from the planned location) of the implanted seeds. Step 504 involves tracking the pathway of the seeds, not just the seeds themselves. In other words, the air gaps are also included, and step 504 does not discriminate the seeds from the air gaps. Step 504 uses the grayscale information the region of interest (ROI), such as the maximum value of a hyper-echoic spot, the mean and the standard deviation of the ROI, the contrast defined by the maximum value divided by the mean, etc.

In step 504, a center and the size of an ROI are preset. That operation can be manually done by the operator by clicking the mouse on the hyper-echoic spots at any z-position or automatically done by using the information from the treatment plan. Thresholding and analysis are then used to determine whether there is a hyper-echoic spot in the ROI. It there is, the ROI center of the next image in the series is switched to the current center position. If not, the previous center is kept.

Figure 9A:
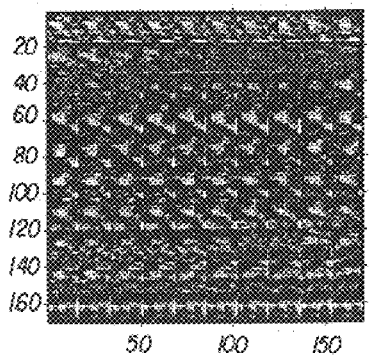
FIGS. 9A and 9B show a sequence of images taken in a column and an identification of those images having hyperechoic spots, respectively.
Figure 9B:
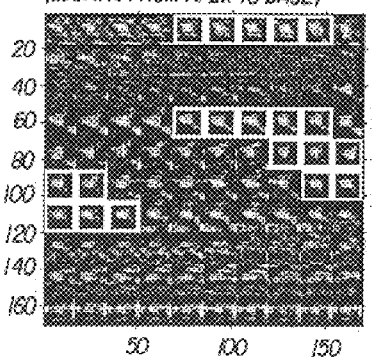

FIG. 9A shows a column of images taken along the pathway corresponding to grid coordinates 12 in the grid 302 of FIG. 3. FIG. 9B shows the same column of images, with boxes identifying the images in which hyperechoic spots have been identified. As shown in FIG. 9B, each hyperechoic spot occupies five consecutive images because of the dimensions of the seed relative to the interval at which the images are taken; an illustrative example of the relevant dimensions will be given below.

Figure 10:
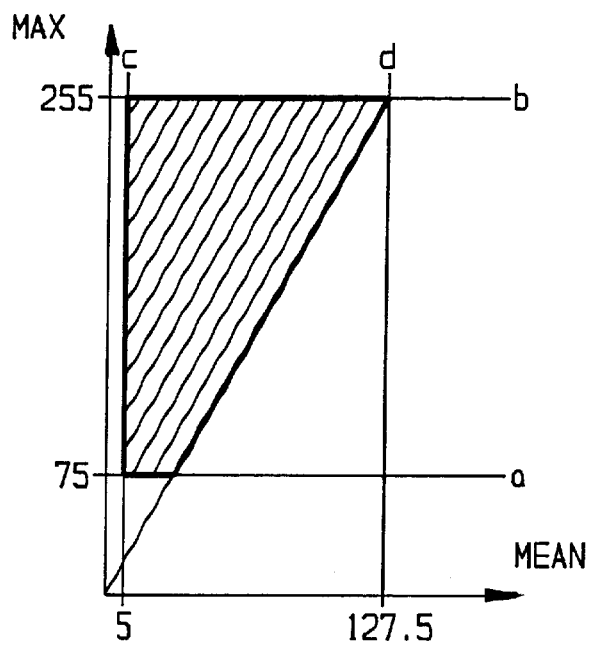
FIG. 10 shows a plot of a threshold used to locate the hyperechoic spots.

The threshold measurement based on the grayscale analysis of the ROI can be illustrated by FIG. 10. For the sake of clarity of illustration, FIG. 10 shows only the maximum, mean, and contrast measurements because they can be shown in a 2-D plot. FIG. 10 is not drawn to scale, and the parameters are examples only, used to make the illustration more intuitive.

The ROI whose grayscale features fall in the shadow area of FIG. 10 is identified as an ROI containing a hyper-echoic spot. In the figure, the four borders of the shadow area are represented with four lines a, b, c, and d, respectively. The lines a and b indicate that the maximum value of the ROI should be between grayscale levels 75 and 255. The line c indicates that the mean value of the ROI should be greater than 5. The line d indicates that the contrast (the slope of the line in the 2-D coordinate system constructed by the mean and maximum) should be greater than 2.

In practice, the line d may be replaced by a curve e (the dotted curve in FIG. 10), which delimits the border more accurately. That is because variations of the mean and the contrast may result in different thresholds. Generally speaking, the greater the mean, the smaller the threshold. As a result, curve e is in the form as shown in the figure. The curve e can be implemented as a curve equation or as a look-up table for correlating the threshold to the mean.

Extending the illustrative example of FIG. 10 to more measurement parameters results in a multi-dimensional space and a shadowed sub-space similar to the shadow area in the 2-D space in FIG. 10.

Step 506, detecting the real z-position of each seed placed along the needle track, is in fact a task of cutting the seed pathway into several segments by discriminating the spots representing seeds from any spots representing air gaps. The grayscale information cannot be used to achieve that goal because some stronger air gaps have greater measurement values than weak seeds, as will be explained below with reference to FIG. 11B. Therefore, a wave form analysis method is used instead.

Figure 11A:
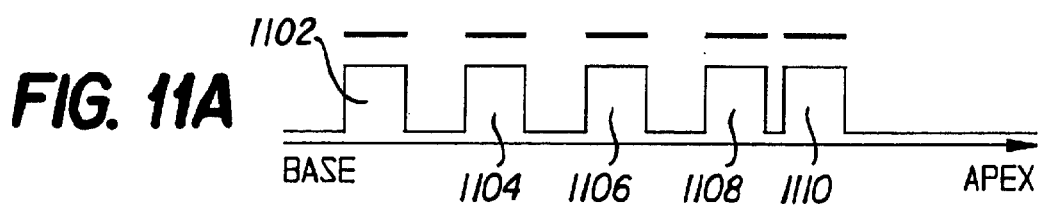
FIGS. 11A and 11B show ideal and typical plots, respectively, of brightness along a needle path.

To simplify the illustration, it is assumed that the distance between two contiguous images is 0.5 mm, so that one seed can occupy at most 10 images in the series, and it usually occupies fewer than 10 due to its slant. Thus, in a case in which the gland has a length of 4.5 cm, the offset is 5 mm, and there are 5 seeds with special spacing, i.e, no spacer, at the apex, an ideal waveform of a needle track should have the appearance shown in FIG. 11A, having rectangular peaks 1102, 1104, 1106, 1108 and 1110 indicating the seeds. However, a real waveform is more likely to have the appearance shown in FIG. 11B, having irregular peaks 1112, 1114, 1116, 1118 and 1120 indicating the seeds.

Figure 11B:
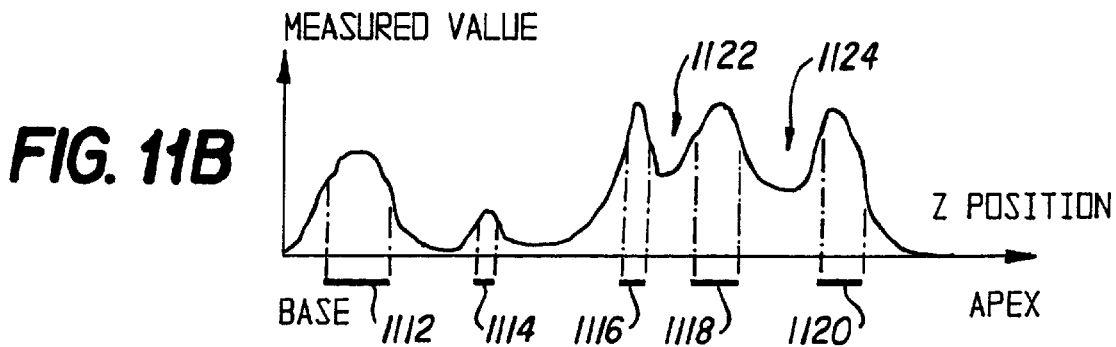

It can be seen in FIG. 11B that although the measured value (MV) of the second peak 1114 is less than that of the air gap 1122 between the peaks 1116 and 1118 or that of the air gap 1124 between the peaks 1118 and 1120, the second peak 1114 has a wave form of peak, while each of the air gaps 1122 and 1124 has the wave form of valley. That distinction between peaks and valleys can be used to discriminate the seeds from the air gaps.

Since it is already known how many seeds are placed in the needle track, the positions of the top several peaks are identified as the centers of seeds. In the case of FIG. 11B, if the plan has four seeds, their positions are taken as the peaks 1112, 1116, 1118 and 1120, but not 1114.

That principle is simple, while the difficulty is the representation of the MV. Since any single grayscale measurement cannot reflect the whole feature of the ROI, it is natural to use their linear combination as the final MV, i.e., $$MV = \Sigma \alpha_i v_i,$$

in which $v_i$ represents each feature such as maximum, contrast, and standard deviation, etc, and $\alpha_i$ represents the coefficient of each feature. Of course, the combination of those features is not constrained to the linear composition, which is the simplest one. Simple least square statistics will determine the value and the confidence interval for each coefficient.

Figures 12A, 12B, 12C:
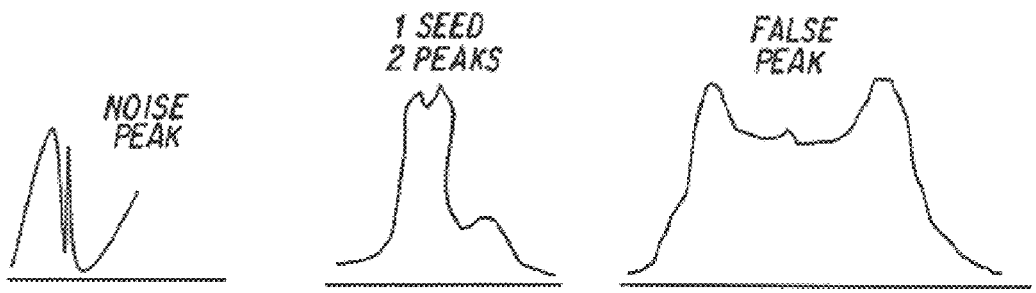
FIGS. 12A–12C show three types of peaks which may occur in image data.

Of course, the MV waveform should be smoothed before it can be processed because the raw signal may contain many noise peaks, as shown in FIG. 12A. Next, the false peaks are removed. For example, if two peaks have a distance less than 6 units along the z-axis, they most likely represent the same seed, so one of them will be absorbed by the other, stronger one, as shown in FIG. 12B. If a peak lies between two other higher peaks and has no distinct drop off before and after it, it is most likely noise, as shown in FIG. 12C.

After those adjustments to the waveform, the peaks are detected to determine how many peaks there are. If the number is greater than the implanted number N of seeds, only the highest N peaks are taken as the seeds, as explained above with reference to FIG. 11B. If the number is less than N, either seed identification is forced using second-tier peaks (with reduced confidence), or the preset transverse size of the ultrasound column is changed to process a larger needle track that includes the exact number of the implanted seeds.

Figure 13A:
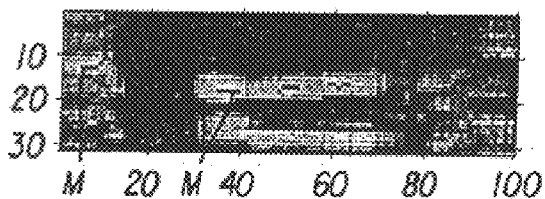
FIGS. 13A–13D show the locations of seeds in image data.
Figure 13B:
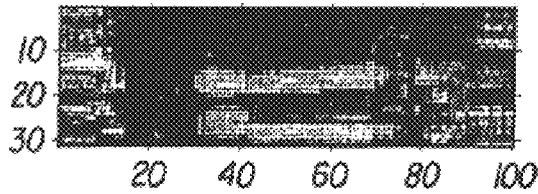
Figure 13C:
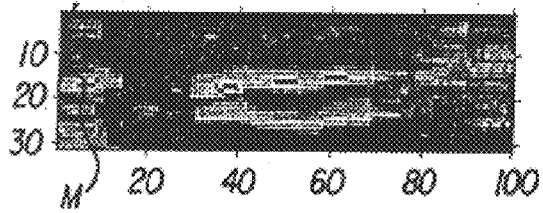
Figure 13D:
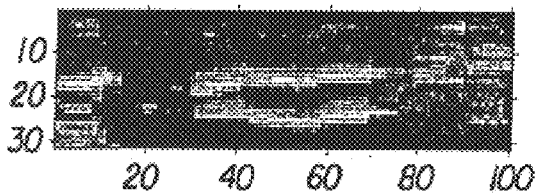

FIGS. 13A–13D show sample seed identifications along grid location 12. In FIGS. 13A and 13C, the seeds are identified by black marks M, while in FIGS. 13B and 13D, they are left unmarked.

Each seed identified in that manner is assigned a confidence level according to the MV level and the fall-off characteristics of the peak. The greater the MV level and the fall off of the peak, the more likely it is a seed. The locations of the seeds and their confidence values are convoluted into subsequent dosimetry calculations, which result in a confidence level for each of the dosimetry parameters arising from the dose-volume histogram, including, D100, D95, D90, D80 and D50.

If the confidence on the chosen dosimetry parameter (currently D90) is acceptably high, seed localization is said to be reliable enough for re-planning and re-optimization of dosimetry, in order to compensate for the dosimetric impact of the aggregate seed misplacements. If the confidence on the chosen dosimetry parameter is not sufficiently high, simple Baysian statistics are used to determine which seed localizations require increased confidence to achieve acceptable confidence in dosimetry. Repeat ultrasound scans are acquired; imaging data for the given needle column(s) are fused using redundant information but with increased signal-to-noise ratio. The above-described process is repeated starting from active seed pathway tracking and ending with dosimetry confidence analysis.

If repeated application of the above process still cannot achieve acceptable dosimetry confidence, x-ray imaging of the seeds will be used to increase the localization confidence of the given seeds. Ultrasound-based seed identification of high confidence values will be used as "anchors" (fiducial marks) to register the ultrasound and x-ray spaces. The coordinates of the low confidence seed localizations will then be corrected using the x-ray projection(s). The confidence values are increased by a variable based on the degree of seed overlap on the x-ray image, the quality of the overall registration, and the quality of the x-ray itself for seed localization.

While a preferred embodiment of the present invention has been set forth above in detail, those skilled in the art who have reviewed the present disclosure will readily appreciate that other embodiments can be realized within the scope of the present invention. For example, the numerical values set forth above should be construed as illustrative rather than limiting. The same is true of the arrangement of the user interface of FIG. 3. Therefore, the present invention should be construed as limited only by the appended claims.

We claim:

1. A method for identifying and quantifying departures in placement of needles or catheters from intended placements in a treatment plan for treating a bodily organ, the needles or catheters carrying seeds for insertion into the bodily organ for use in the treatment plan, the method comprising:

(a) inserting the needles or catheters into the bodily organ, so as to deposit the seeds, and inputting actual placements into an intraoperative tracking interface;

(b) for at least one needle or catheter carrying seeds, calculating a difference between an intended placement of that needle or catheter and the actual placement of that needle or catheter;

(c) calculating, from the difference calculated in step (b), a position error for each of the seeds; and (d) recalculating a dosimetry associated with at least one of the seeds in accordance with the position error calculated in step (c).

2. The method of claim 1, wherein step (b) comprises receiving, through the intraoperative tracking interface, a selection by an operator of a needle or catheter.

3. The method of claim 1, further comprising a step of displaying, on the intraoperative tracking interface, at least one isodose plot of the bodily organ.

4. The method of claim 1, wherein said imaging in step (e) is through real-time ultrasound imaging of the bodily organ.

5. The method of claim 4, wherein:

step (e) comprises receiving, through the intraoperative tracking interface, a selection by an operator of a needle or catheter; and the real-time ultrasound imaging in step (e) is in a direction of the needle or catheter selected by the operator.

6. The method of claim 5, wherein the real-time ultrasound imaging includes creating a column of ultrasound images along the needle or catheter selected by the operator.

7. The method of claim 6, wherein step (e) further comprises gray-scale preprocessing of the column of ultrasound images.

8. The method of claim 7, wherein the gray-scale preprocessing renormalizes a gray-scale histogram of ultrasound images to produce gray-scale corrected ultrasound images.

9. The method of claim 8, wherein the gray-scale corrected ultrasound images are used to find locations of the seeds along the needle or catheter selected by the operator.

10. The method of claim 9, wherein a number of seeds whose locations are found in the gray-scale corrected ultrasound images is compared to a number of seeds which were actually deposited by the needle or catheter selected by the operator.

11. The method of claim 10, wherein, when the numbers of seeds are not equal, at least one dimension of the column of ultrasound images is changed, the column of ultrasound images is reconstructed or reacquired, the reconstructed or reacquired column of ultrasound images undergoes the gray-scale preprocessing to renormalize the gray-scale histogram of the reconstructed or reacquired column of ultrasound images to produce additional gray-scale corrected ultrasound images which are used to find the locations along the seeds along the needle or catheter selected by the operator, and a number of seeds whose locations are found in the additional gray-scale corrected ultrasound images is compared to the number of seeds which were actually deposited by the needle or catheter selected by the operator.

12. The method of claim 9, wherein the locations of the seeds found in the gray-scale corrected ultrasound images are used for further correction of the positions of the seeds.

13. The method of claim 1, wherein the bodily organ is a prostate.

14. The method of claim 1, further comprising:

(e) depositing a number of the seeds and determining positions of the deposited number of the seeds through imaging; and (f) recalculating a dosimetry associated with at least one of the seeds deposited in step (e).

15. The method of claim 14, further comprising (g) assigning a confidence level to each of the positions determined in step (e), and wherein step (f) comprises recalculating the dosimetry associated with each of the seeds whose confidence levels exceed a predetermined threshold.

16. The method of claim 15, further comprising:

(h) adjusting positions of the seeds having low confidence values assigned in step (g) in accordance with x-ray imaging;

(i) recalculating a dosimetry associated with all of the seeds; and (j) assigning a confidence level to the dosimetry recalculated in step (i).

17. The method of claim 1, wherein step (b) comprises calculating the difference in an x-y plane.

18. A system for identifying and quantifying departures in the placement of needles or catheters from intended placements in a treatment plan for treating a bodily organ, the needles or catheters carrying seeds for insertion into the bodily organ for use in the treatment plan, the system comprising:

an imaging device for imaging the bodily organ;

an intraoperative tracking interface comprising a display; and a computing device, in electronic communication with the imaging device and the intraoperative tracking interface, for:

(a) receiving an input of actual placements into the intraoperative tracking interface;

(b) for at least one needle or catheter, calculating a difference between an intended placement of that needle or catheter and the actual placement of that needle or catheter;

(c) calculating, from the difference calculated in step (b), a position error for each of the seeds; and (d) recalculating a dosimetry associated with at least one of the seeds in accordance with the position error calculated in step (c).

19. The system of claim 18, wherein the intraoperative tracking interface comprises an input device which permits the operator to select a needle or catheter for step (b).

20. The system of claim 18, wherein the computing device is programmed to control the intraoperative tracking interface to display at least one isodose plot of the bodily organ.

21. The system of claim 18, wherein:

the imaging device comprises a real-time ultrasound imaging device; and the computing device performs step (e) through real-time ultrasound imaging of the bodily organ by the real-time ultrasound imaging device.

22. The system of claim 21, wherein:

the intraoperative tracking interface permits an operator to select a needle or catheter; and the real-time ultrasound imaging is performed in a direction of the needle or catheter selected by the operator.

23. The system of claim 22, wherein the real-time ultrasound imaging results in a column of ultrasound images along the needle or catheter selected by the operator.

24. The system of claim 21, wherein the real-time ultrasound imaging creates a column of ultrasound images, and wherein the computing device is programmed to perform gray-scale preprocessing on the column of ultrasound images.

25. The system of claim 24, wherein the computing device is programmed such that the gray-scale preprocessing renormalizes a gray-scale histogram of the column of ultrasound images to produce gray-scale corrected ultrasound images.

26. The system of claim 25, wherein the gray-scale corrected ultrasound images are used to find locations of the seeds along the needle or catheter selected by the operator.

27. The system of claim 26, wherein the locations of the seeds found in the gray-scale corrected ultrasound images are used for further correction of the positions of the seeds.

28. The system of claim 25, wherein the computing device is programmed to use the gray-scale corrected ultrasound images to find locations of the seeds along the needle or catheter selected by the operator, and to compare a number of seeds whose locations are found in the gray-scale corrected ultrasound images to a number of seeds which were actually deposited by the needle or catheter selected by the operator.

29. The system of claim 28, wherein the computing device is programmed such that, when the numbers of seeds are not equal, at least one dimension of the column of ultrasound images is changed, and the column of ultrasound images is reconstructed or reacquired, the reconstructed or reacquired column of ultrasound images undergoes the gray-scale preprocessing to renormalize the gray-scale histogram of the reconstructed or reacquired column of ultrasound images to produce additional gray-scale corrected ultrasound images which are used to find the locations along the seeds along the needle or catheter selected by the operator, and a number of seeds whose locations are found in the additional gray-scale corrected ultrasound images is compared to the number of seeds which were actually deposited by the needle or catheter selected by the operator.

30. The system of claim 18, wherein, when a number of the seeds are deposited, the computing device also performs the following:
    (e) determining positions of the deposited number of the seeds through imaging; and
    (f) recalculating a dosimetry associated with at least one of the seeds deposited in step (e).

31. The system of claim 30, wherein the computing device also performs (g) assigning a confidence level to each of the positions determined in step (e), and wherein step (f) performed by the computing device comprises recalculating the dosimetry associated with each of the seeds whose confidence levels exceed a predetermined threshold.

32. The system of claim 31, wherein the imaging device comprises an x-ray imaging device, and wherein the computing device further performs the following:
    (h) adjusting positions of the seeds having low confidence values assigned in step (g) in accordance with x-ray imaging carried out through the x-ray imaging device;
    (i) recalculating a dosimetry associated with all of the seeds; and
    (j) assigning a confidence level to the dosimetry recalculated in step (i).

33. The system of claim 18, wherein the computing device calculates the difference in an x-y plane.

* * * * *